(12) United States Patent
Lambert et al.

(10) Patent No.: US 8,277,728 B2
(45) Date of Patent: *Oct. 2, 2012

(54) METHOD OF STERILIZING AN ORTHOPAEDIC IMPLANT

(75) Inventors: Richard D. Lambert, Germantown, TN (US); Terry W. McLean, Cordova, TN (US); David B. Vogel, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,342

(22) Filed: Sep. 19, 2011

(65) Prior Publication Data

US 2012/0000058 A1   Jan. 5, 2012

Related U.S. Application Data

(60) Continuation of application No. 13/017,943, filed on Jan. 31, 2011, now Pat. No. 8,025,841, which is a continuation of application No. 11/615,127, filed on Dec. 22, 2006, now Pat. No. 7,947,220, which is a division of application No. 10/914,551, filed on Aug. 9, 2004, now Pat. No. 8,100,984.

(60) Provisional application No. 60/493,247, filed on Aug. 7, 2003.

(51) Int. Cl.
| | |
|---|---|
| A61L 2/08 | (2006.01) |
| A61L 9/00 | (2006.01) |
| A61L 2/00 | (2006.01) |
| B08B 9/00 | (2006.01) |
| B08B 3/00 | (2006.01) |
| A61F 2/32 | (2006.01) |
| A61F 2/60 | (2006.01) |
| A61F 2/80 | (2006.01) |
| A61F 2/24 | (2006.01) |
| A61F 5/00 | (2006.01) |
| A61B 17/56 | (2006.01) |

(52) U.S. Cl. ............... 422/28; 422/26; 422/32; 422/34; 134/22.15; 134/30; 134/31; 623/22.21; 623/22.24; 623/22.25; 623/22.32; 623/22.38; 623/22.39; 623/22.42; 623/22.43; 623/22.13; 623/33.34; 606/53; 606/56; 606/249; 606/302; 606/303; 606/304; 606/91

(58) Field of Classification Search ............... 422/1, 26, 422/28, 32, 34, 298, 305, 36–37; 134/22.15, 134/30–31; 623/920, 923, 11.11–66.1; 606/53, 606/56, 249, 302–304, 91

See application file for complete search history.

(56) References Cited

U.S. PATENT DOCUMENTS 3,608,096 A   9/1971   Link
(Continued)

FOREIGN PATENT DOCUMENTS

EP   1369094   12/2003
(Continued)

OTHER PUBLICATIONS

Sigholm et al., Graft perforations favor osteoinduction, studies of rabbit cortical grafts sterilized with ethylene oxide, Acta Orthop. Scand. 63(2):177-182 (1992).

(Continued)

*Primary Examiner* — Jill Warden
*Assistant Examiner* — Monzer Chorbaji
(74) *Attorney, Agent, or Firm* — Ropes & Gray LLP

(57) ABSTRACT

A pre-assembled orthopaedic implant adapted for improved gas sterilization. The implant includes a first component adapted for assembly with a second component such that a mating surface of the first component is in close proximity with a mating surface of the second component. At least one gas conduit associated with the mating surface of the first component facilitates a sterilizing gas to penetrate into and dissipate from the interface defined by the mating surfaces.

11 Claims, 3 Drawing Sheets

U.S. PATENT DOCUMENTS

| | | | |
|---|---|---|---|
| 3,818,514 A | | 6/1974 | Clark |
| 3,840,904 A | | 10/1974 | Tronzo |
| 3,882,550 A | | 5/1975 | Karpf et al. |
| 3,903,549 A | | 9/1975 | Deyerle |
| 4,550,546 A | | 11/1985 | Raley et al. |
| 4,664,058 A | | 5/1987 | Schroeder et al. |
| 4,714,477 A | * | 12/1987 | Fichera et al. .............. 623/22.19 |
| 4,976,731 A | | 12/1990 | Perry |
| 5,019,105 A | | 5/1991 | Wiley |
| 5,059,209 A | | 10/1991 | Jones |
| 5,080,677 A | * | 1/1992 | Shelley ....................... 623/22.24 |
| RE33,854 E | | 3/1992 | Adair |
| 5,139,497 A | | 8/1992 | Tilghman et al. |
| 5,246,462 A | | 9/1993 | Bekki et al. |
| 5,350,300 A | | 9/1994 | Gallais |
| 5,480,448 A | | 1/1996 | Mikhail |
| 5,547,635 A | | 8/1996 | Duthie, Jr. |
| 5,577,368 A | | 11/1996 | Hamilton et al. |
| 5,641,323 A | | 6/1997 | Caldarise |
| 5,681,322 A | | 10/1997 | Hartigan, Jr. |
| 5,702,476 A | | 12/1997 | Limacher et al. |
| 5,716,413 A | | 2/1998 | Walter et al. |
| 5,732,821 A | | 3/1998 | Stone et al. |
| 5,782,927 A | | 7/1998 | Klawitter et al. |
| 6,110,205 A | | 8/2000 | Nies |
| 6,152,962 A | | 11/2000 | DeCarlo, Jr. |
| 6,242,507 B1 | | 6/2001 | Saum et al. |
| 6,268,048 B1 | | 7/2001 | Topolkaraev et al. |
| 6,403,033 B1 | | 6/2002 | Gutman |
| 6,500,386 B1 | | 12/2002 | Burstein |
| 6,889,839 B1 | | 5/2005 | Rosten et al. |
| 6,986,792 B2 | | 1/2006 | McLean et al. |
| 7,302,784 B2 | | 12/2007 | Harges et al. |
| 7,947,220 B2 | * | 5/2011 | Lambert et al. .................... 422/1 |
| 8,025,841 B2 | * | 9/2011 | Lambert et al. ................. 422/28 |
| 2002/0068980 A1 | | 6/2002 | Serbousek et al. |
| 2002/0120342 A1 | | 8/2002 | Gibbs |
| 2002/0168289 A1 | * | 11/2002 | McVey ........................... 422/28 |
| 2003/0009230 A1 | | 1/2003 | Gundlapalli et al. |
| 2003/0114935 A1 | | 6/2003 | Chan et al. |
| 2003/0177819 A1 | | 9/2003 | Maale |
| 2004/0019380 A1 | * | 1/2004 | Baege et al. ................ 623/11.11 |
| 2005/0102033 A1 | | 5/2005 | Lambert |
| 2005/0261777 A1 | | 11/2005 | Jones et al. |
| 2006/0149285 A1 | | 7/2006 | Burgi et al. |
| 2007/0088442 A1 | | 4/2007 | Cima et al. |
| 2007/0122305 A1 | | 5/2007 | Lambert et al. |
| 2007/0219412 A1 | | 9/2007 | DiGiovanni et al. |
| 2007/0249899 A1 | | 10/2007 | Seifert |

FOREIGN PATENT DOCUMENTS

| | | |
|---|---|---|
| JP | 1221164 | 9/1989 |
| JP | 04044756 | 2/1992 |
| WO | WO99/59500 | 11/1999 |
| WO | WO03/049930 | 6/2003 |
| WO | WO2005/013865 | 2/2005 |
| WO | WO2008/100541 | 2/2008 |

OTHER PUBLICATIONS

Notice of Allowance dated Oct. 13, 2011 in U.S. Appl. No. 10/914,551.

* cited by examiner

METHOD OF STERILIZING AN ORTHOPAEDIC IMPLANT

CROSS-REFERENCE TO RELATED APPLICATIONS

This application is a continuation of U.S. patent application Ser. No. 13/017,943 filed on Jan. 31, 2011, now U.S. Pat. No. 8,025,841, which is a continuation of U.S. patent application Ser. No. 11/615,127 filed on Dec. 22, 2006, now U.S. Pat. No. 7,947,220, which is a divisional of U.S. patent application Ser. No. 10/914,551 filed on Aug. 9, 2004, now U.S. Pat. No. 8,100,984, which claims the benefit of U.S. Provisional Application No. 60/493,247, filed Aug. 7, 2003 and entitled "Modified Orthopaedic Implants for Improved Sterilization." The disclosure of each application is incorporated by reference in its entirety.

STATEMENT REGARDING FEDERALLY SPONSORED RESEARCH OR DEVELOPMENT

Not Applicable.

Appendix.

Not Applicable.

BACKGROUND OF THE INVENTION

1. Field of the Invention

Embodiments of the present invention relate to pre-assembled orthopaedic implants adapted for gas sterilization.

2. Related Art

Orthopaedic implants, such as knee, hip or shoulder prostheses, occasionally include components that are shipped to the surgeon or other user in a pre-assembled condition. For example, a hip prosthesis may include a bipolar component that includes a metal acetabular shell pre-assembled with a plastic liner. To lessen the chances of post-implantation failure, the shell and liner must fit together snugly, with a relatively tight interface between the two components.

Pre-assembled components, as well as other orthopaedic implant components, may be sterilized prior to use to minimize the chances of infection. Orthopaedic components may be sterilized using a number of different techniques, including gas sterilization and gamma radiation.

In some circumstances, gas sterilization is a preferred technique for sterilizing orthopaedic components. Gas sterilization utilizes a gas such as ethylene oxide (ETO) or vaporized hydrogen peroxide (VHP) to incapacitate bacterial or other disease causing agents. However, gas sterilization May be ineffective in certain circumstances. For example, if during sterilization the gas is unable to contact all surfaces of the orthopaedic components, it may not effectively sterilize those components.

Typical pre-assembled orthopaedic components may not be suitable for gas sterilization. Because of the relatively tight interface between the components, the gas may not be able to penetrate between the components to sterilize all of the surfaces. Additionally, even if some of the gas penetrates between the pre-assembled components, the gas may not necessarily be able to effectively dissipate from in between the tightly fitted pre-assembled components after sterilization is complete. Trace amounts of gas may remain in the implant, potentially having deleterious effects on the health of the individual who receives the implant.

Because typical pre-assembled orthopaedic implants may not be suitable for gas sterilization, they have in the past been sterilized using the less preferable gamma irradiation technique. Gamma irradiation may cause oxidation of plastics, such as the polyethylene commonly used for the plastic liner of a pre-assembled orthopaedic component. Oxidation of the polyethylene forming the plastic liner may weaken the component, increasing the chance that the implant will fail. Gamma irradiation may also be undesirable because it may neutralize the effects of cross-linking in highly cross-linked plastic components, also potentially weakening the component.

SUMMARY OF THE INVENTION

Various embodiments of the present invention include a pre-assembled orthopaedic implant suitable for gas sterilization. In some embodiments, one or more gas conduits associated with one or more of the orthopaedic components facilitates the penetration and/or dispersion of a sterilizing gas into and from the pre-assembled components, but do not affect the mechanical integrity or overall performance of the implant. Embodiments of the present invention may include pre-assembled knee, hip, shoulder or other orthopaedic components.

In accordance with embodiments of the present invention, the gas conduit or conduits may be formed in several suitable shapes, sizes, locations, orientations or configurations. For example, in some embodiments the gas conduits are a plurality of channels inscribed onto a mating surface of one or more of the orthopaedic components. In other embodiments, the gas conduits are one or more apertures passing through one or more of the orthopaedic components. Other embodiments may include any combination of the foregoing gas conduits, or other structures serving as suitable gas conduits.

Further features, aspects, and advantages of the present invention, as well as the structure and operation of various embodiments of the present invention, are described in detail below with reference to the accompanying drawings.

DETAILED DESCRIPTION OF THE EMBODIMENTS

Figure 1:
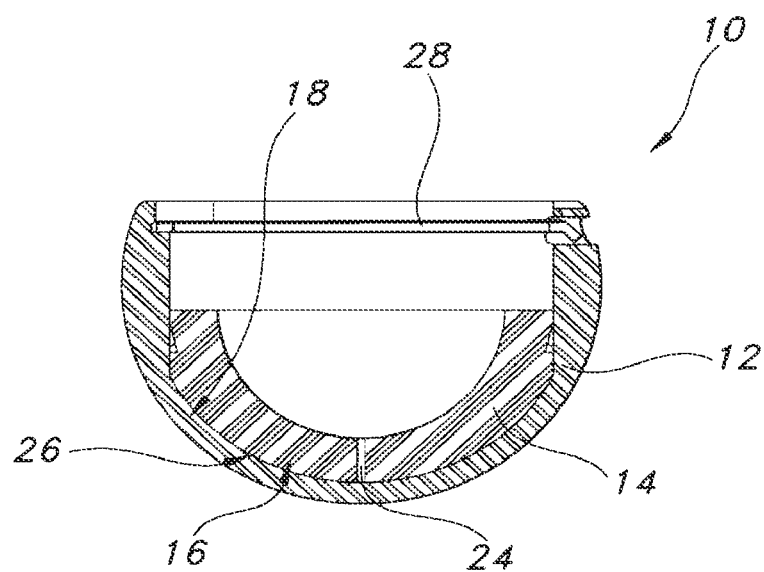
FIG. 1 shows a schematic cross-sectional view of a orthopaedic implant shown in a pre-assembled condition in accordance with a first embodiment of the present invention.
Figure 5:
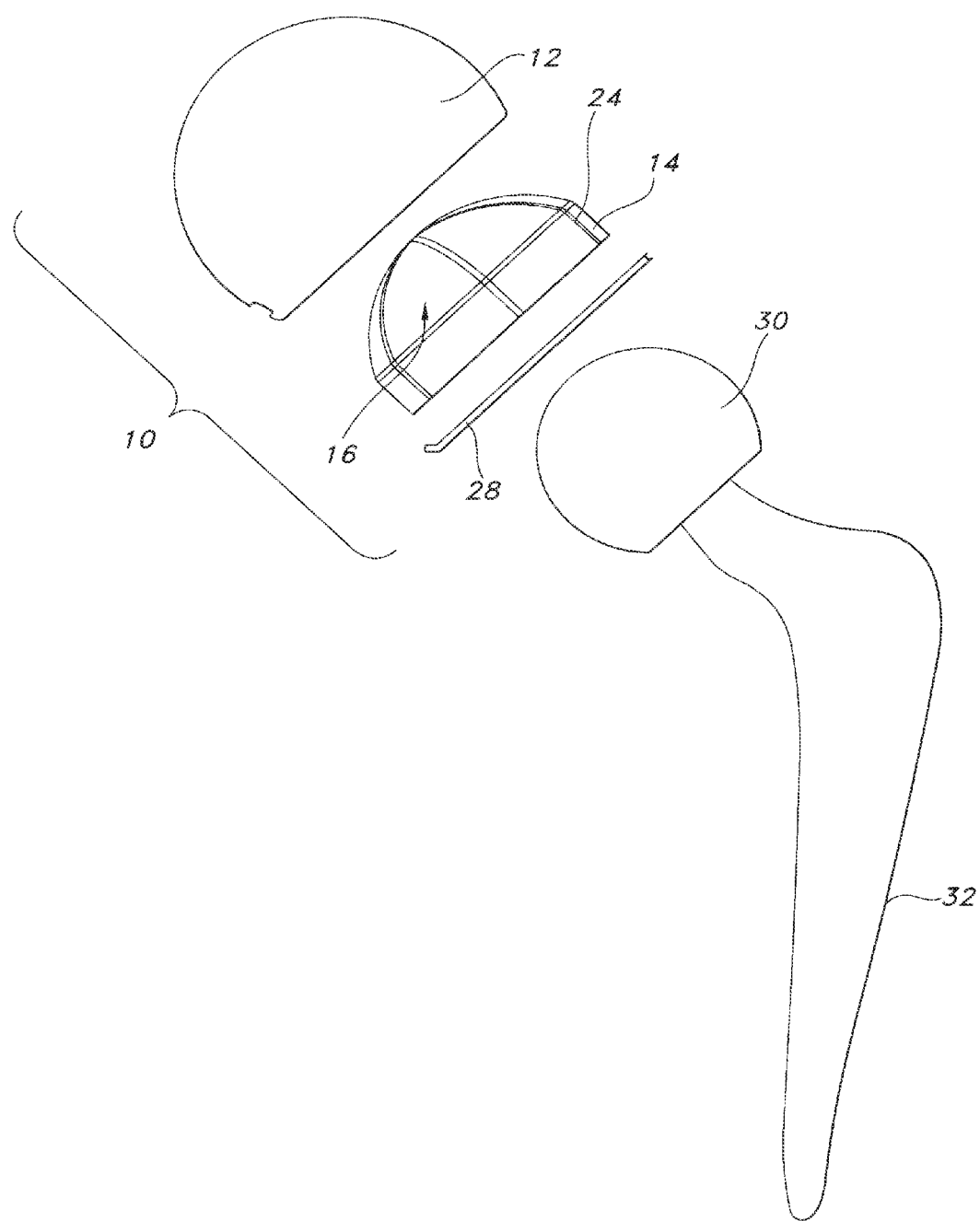
FIG. 5 shows a schematic view of an orthopaedic hip implant in accordance with another embodiment of the present invention, shown in a disassembled state.

Referring to the accompanying drawings in which like reference numbers indicate like elements, FIG. 1 shows an orthopaedic implant 10 according to a first embodiment of the present invention. The implant 10 shown in FIG. 1 is adapted for implantation into the acetabulum of a hip such that the implant 10 can receive a prosthetic femoral head in a rotating fashion (however, embodiments of the present invention also include implants that can interact with natural portions of the anatomy—such as natural femoral heads). FIG. 5 shows (in a disassembled state) implant 10 associated with a femoral head 30 and stem 32.

As shown in FIG. 1, orthopaedic implants 10 in accordance with embodiments of the present invention may include at least two orthopaedic components 12 and 14. FIG. 1 shows the implant including two components: an acetabular shell 12 and a liner 14. In the embodiment shown in FIG. 1, acetabular shell 12 is metal and liner 14 is a plastic, such as ultra high molecular weight polyethylene. However, shell 12 and liner 14 may be formed from any desirable material.

Implant 10 be assembled by press fitting liner 14 into an interior cavity of acetabular shell 12 such that a mating surface 16 on the liner 14 is in close proximity with a mating surface 18 of the acetabular shell 12, defining a mating surface interface 26. Liner 14 may be secured in shell 12 in any desirable, conventional, or non-conventional manner.

Implant 10 may be shipped with the liner 14 assembled in the shell 12 and may be sterilized after assembly. If necessary or desired, the pre-assembled implant 10 may be later combined with other components to finalize assembly of the implant prior to implantation. A retaining ring 28 may secure the additional component to the pre-assembled implant.

Pre-assembled implant 10 may include one or more gas conduits 24. Gas conduits 24, as discussed above, may permit sterilization gasses such as ETO or VHP to penetrate into the mating surface interface 26, between the mating surfaces 16 and 18 of the shell 12 and liner 14. Gas conduits 24 may also facilitate dispersion of the sterilization gas from in-between the mating surfaces 16 and 18 of the components after sterilization is complete. Gas conduits 24 may be formed as one or more channels, one or more apertures, any combination of channels and apertures, or any other desired structure. The gas conduits 24 may be formed by machining, molding or any other conventional or non-conventional technique.

Figure 2:
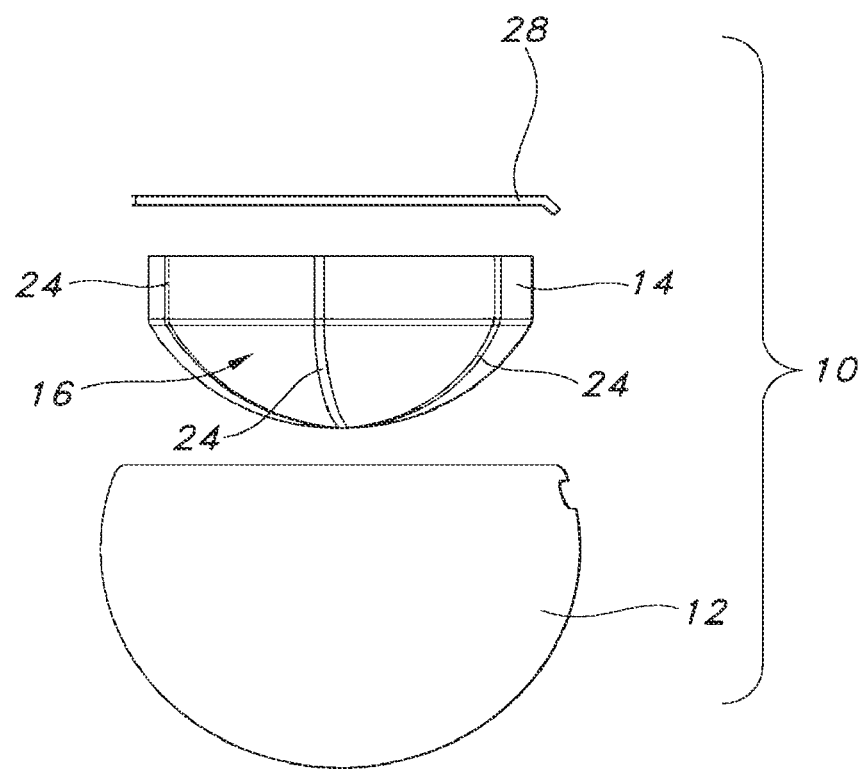
FIG. 2 shows a schematic view of the pre-assembled orthopaedic implant shown in FIG. 1 in a disassembled condition.

FIG. 1 shows an aperture gas conduit 24 extending from an inner surface to the outer, mating surface 16 of the liner. FIG. 2 shows a plurality of channel gas conduits 24 engraved in the mating surface 16 of the liner. In some embodiments, the liner may include both channels and apertures as gas conduits.

Figure 4:
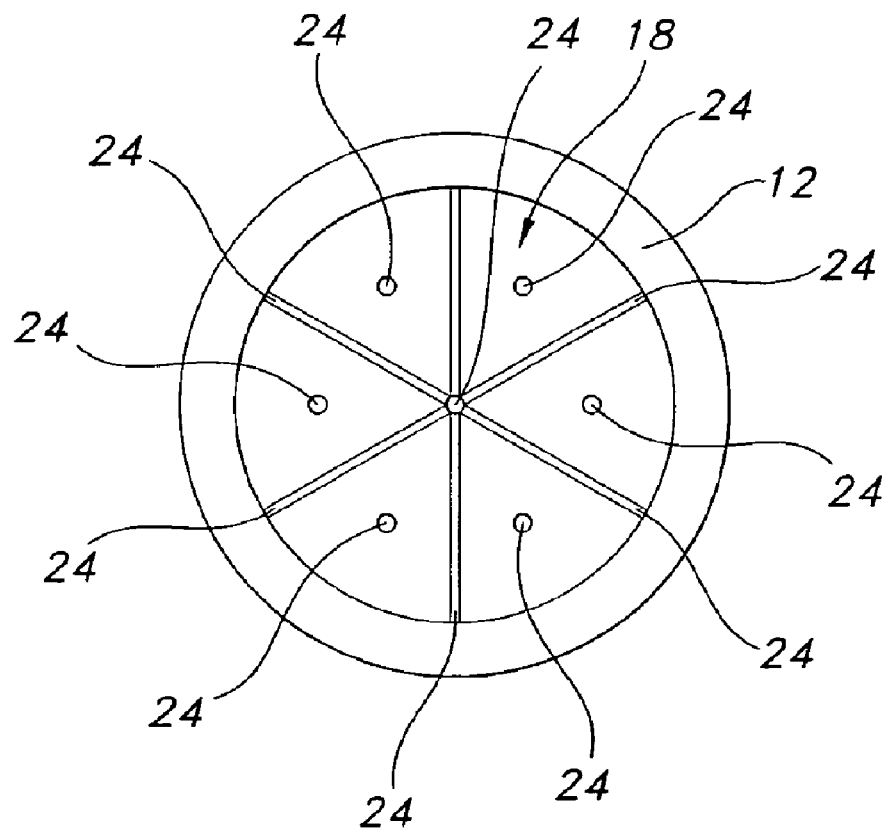
FIG. 4 shows a schematic view of an orthopaedic component in accordance with another embodiment of the present invention.

In still other embodiments, such as the embodiment shown in FIG. 4, the acetabular shell 12 may also include gas conduits 24, such as apertures and channels. Gas conduits 24 associated with the acetabular shell 12 may facilitate the penetration and subsequent dispersion of sterilizing gas in a similar manner to gas conduits 24 associated with the liner 14.

Figure 3:
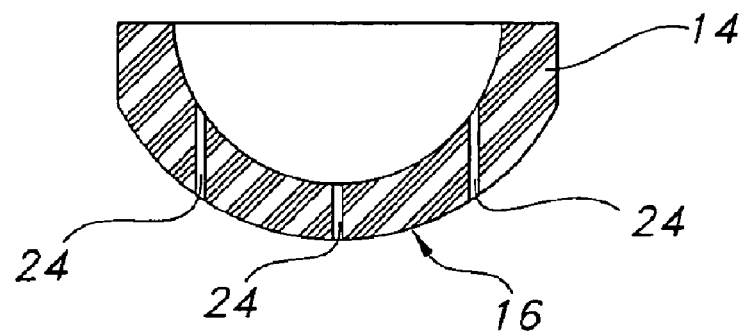
FIG. 3 shows a schematic cross-sectional view of an orthopaedic component in accordance with another embodiment of the present invention.

Gas conduits 24 may be associated with the shell 12, liner 14, or both, in any desired number, position or orientation to maximize the facilitation of penetration and dispersion of sterilizing gas between the mating surfaces 16 and 18 of the acetabular shell 12 and liner 14. For example, in the embodiment shown in FIGS. 1 and 2, the acetabular liner 14 includes three channels forming arcs on the surface of the liner 14 and one aperture at an apex of the liner 14. Alternatively, as the embodiment in FIG. 3 shows, there are multiple apertures extending through the acetabular liner 14. In the alternate embodiment shown in FIG. 4, multiple channels and multiple apertures are associated with the acetabular shell 14.

As those skilled in the art will appreciate, the particular embodiment of this invention described above and illustrated in the figures is provided for explaining the invention, and various alterations may be made in the structure and materials of the illustrated embodiment without departing from the spirit and scope of the invention as described above. For example, orthopaedic implants in accordance with the present invention are not limited to acetabular shells and liners. Pre-assembled implants for use with knees, shoulders or other joints of the anatomy may also include gas conduits for improved sterilization in accordance with the embodiments of the present invention.

What is claimed is:

1. A method of sterilizing an orthopaedic implant comprising the steps of:
   a. providing a liner, the liner having a liner mating surface and at least one gas conduit;
   b. providing a shell, the shell having a shell mating surface;
   c. fixing in a final position the liner to the shell to form an orthopedic assembly such that the liner mating surface confronts the shell mating surface to define a mating surface interface; and
   d. subjecting the assembly to a gas sterilization process such that the at least one gas conduit delivers a sterilization gas to substantially penetrate the mating surface interface.

2. The method of sterilizing an orthopaedic implant of claim 1, wherein the step of subjecting the assembly to a gas sterilization process comprises subjecting the assembly to an ethylene oxide gas sterilization process.

3. The method of sterilizing an orthopaedic implant of claim 1, wherein the step of subjecting the assembly to a gas sterilization process comprises subjecting the assembly to a vaporized hydrogen peroxide gas sterilization process.

4. The method of sterilizing an orthopaedic implant of claim 1, wherein the step of assembling the liner to the shell comprises press fitting the liner into the shell.

5. The method of sterilizing an orthopaedic implant of claim 1, further comprising the step of assembling a femoral head to the liner.

6. The method of sterilizing an orthopaedic implant of claim 1, further comprising the steps of:
   a. providing a stem;
   b. assembling a femoral head to the stem; and
   c. assembling the femoral head to the liner.

7. The method of sterilizing an orthopaedic implant of claim 1, further comprising the step of securing the femoral head.

8. The method of sterilizing an orthopaedic implant of claim 1, further comprising the step of assembling a retaining ring to the shell.

9. A method of sterilizing an orthopaedic implant comprising the steps of:
   a. providing a first orthopaedic component, the first orthopaedic component having a first mating surface and at least one gas conduit;
   b. providing a second orthopaedic component, the second orthopaedic component having a second mating surface;
   c. securing the second orthopaedic component to the first orthopaedic component in a final position to form an orthopaedic implant having a mating surface interface defined by the first mating surface and second mating surface; and
   d. subjecting the formed implant to a gas sterilization process such that the at least one gas conduit positions a sterilization gas in contact with the mating surface interface.

10. The method of sterilizing an orthopaedic implant of claim 9, further comprising the steps of:
    a. providing a stem;
    b. assembling a femoral head to the stem; and
    c. assembling the femoral head to the formed implant.

11. The method of sterilizing an orthopaedic implant of claim 9, further comprising the step of assembling a retaining ring to the shell.

* * * * *